US00PP23525P2

(12) United States Plant Patent
Korlipara

(10) Patent No.: US PP23,525 P2
(45) Date of Patent: Apr. 9, 2013

(54) ***ECHINACEA* PLANT NAMED 'ALOHA'**

(50) Latin Name: *Echinacea* spp.
Varietal Denomination: Aloha

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 67 days.

(21) Appl. No.: 13/200,473

(22) Filed: Sep. 22, 2011

(51) Int. Cl.
*A01H 5/00* (2006.01)

(52) U.S. Cl. ..... Plt./428

(58) Field of Classification Search ..... Plt./428
See application file for complete search history.

*Primary Examiner* — Howard Locker
(74) *Attorney, Agent, or Firm* — Klarquist Sparkman, LLP

(57) ABSTRACT

A new and distinct *Echinacea* plant named 'Aloha' characterized by large yellow orange to cream inflorescences, broad, overlapping ray florets, a strong, upright, short habit, strong, well branched stems, and excellent vigor.

1 Drawing Sheet

Botanical denomination: *Echinacea* spp.
Variety designation: 'Aloha'.

The present invention relates to a new and distinct cultivar of *Echinacea* and given the cultivar name 'Aloha'. *Echinacea* is in the family *Asteraceae*. This new cultivar is a fourth generation seeding originating from a planned breeding program using *Echinacea paradoxa* (an unpatented plant) as the seed parent in the original cross and *Echinacea purpurea* 'Ruby Giant' (an unpatented plant) as the pollen parent. The exact parents of this selection are unknown, unnamed, proprietary plants.

Compared to *Echinacea* Harvest Moon™ ('Matthew Saul' U.S. Plant Pat. No. 17,652), the new variety is shorter and has larger inflorescences with has longer and wider ray florets, also the ray florets are held horizontally rather than strongly reflexed.

This new *Echinacea* cultivar is distinguished by:

1. large yellow orange to cream inflorescences,
2. broad, overlapping ray florets,
3. strong, upright, short habit,
4. strong, well branched stems, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows one-year-old plants of *Echinacea* 'Aloha' in full bloom growing in the trial field in full sun in September in Canby, Oreg.

DETAILED PLANT DESCRIPTION

The following is a detailed description of the new *Echinacea* cultivar based on observations of 18-month-old specimens growing in the trial bed in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition.

Plant:

*Type*.—Herbaceous perennial.
*Hardiness*.—USDA Zones 4 to 9.
*Size*.—Grows to about 38 cm wide and 60 cm tall to top of inflorescences.
*Form*.—Basal clump, with about 16 stems from the base.
*Vigor*.—Excellent.
*Roots*.—Fibrous, with many downward growing and few laterals, ivory in color, Yellow White 158D, roots develop easily from cuttings from the crown.

Stem (flowering):

*Type*.—Ascending, with 1 to 6 inflorescences per stem.
*Size*.—To 43 cm tall to a terminal inflorescence and 6 mm wide at base.
*Internode length*.—2 cm to 6 cm.
*Surface texture*.—Strigose.
*Color*.—Yellow Green 146C.

Leaf (basal):

*Type*.—Simple.
*Shape*.—Lanceolate.
*Arrangement*.—Basal.
*Blade size*.—Grows to 15 cm long and 7 cm wide.
*Margins*.—Serrate.
*Apex*.—Acuminate.
*Base*.—Attenuate.
*Surface texture*.—Strigose on both sides.
*Venation*.—Pinnate, with 3 main veins.
*Color*.—Topside Green 137A bottom side Yellow Green 147B.
*Petiole description*.—Grows to 27 cm long and 4 mm wide, strigose, Yellow Green 146C.

Leaf (stem):

*Type*.—Simple.
*Shape*.—Lanceolate.
*Arrangement*.—Alternate.

*Blade size*.—Grows to 10 cm long and 4.3 cm wide.

*Margins*.—Coarsely serrate.

*Apex*.—Acuminate.

*Base*.—Attenuate.

*Surface texture*.—Strigose on both sides.

*Venation*.—Pinnate, with 3 main veins from the base.

*Color*.—Topside Green 137A bottom side Yellow Green 147B.

*Petiole description*.—On lowermost leaves only, clasping, grows to 5 cm long and 2 mm wide above the clasp, strigose, Yellow Green 146C.

Inflorescence:

*Type*.—Composite on terminal stalked heads.

*Number of flowering stems from the ground*.—About 16.

*Flowering stem*.—Grows to 57 cm tall from the base of the plant to the terminal inflorescence and can grow to 9 to 14 cm long from the top stem leaf to the base of an inflorescence; branched with 1 to 6 inflorescences per stem; diameter growing to 8 mm wide near the inflorescence; strigose; Yellow Green 146C.

*Size*.—Grows to 12 cm wide and 4.5 cm deep as disc enlarges.

*Form*.—Ray florets tilt upward when young, then held horizontally with the sides folding down, mature disc is conic.

*Immature inflorescence*.—Grows to 3 cm wide and 3 cm deep, ray florets held upright and rolled up so only the back color shows, Yellow 11C, disc color Green 138A.

*Ray florets*.—Without pistil or stamen, about 20 full size in number, grow to 60 mm long and 19 mm wide, oblanceolate with the tip two -toothed (each acute), entire margins, base attenuate, glabrous on both sides; topside Yellow Orange 17A maturing to Yellow 16C and later to Yellow 11D, bottom side Yellow 13D.

*Disc*.—Flat becoming conic, becoming 25 mm deep and 36 mm wide with maturity, Yellow Green 146A in the background and Orange 24A in the foreground.

*Disc florets*.—About 300 in number, each with 1 pistil and 4 stamen, grow to 10 mm long and 1.5 mm wide, each with one persistent, very stiff linear bract (13 mm long with the top 4 mm colored Yellow Orange 20A on tip then Yellow Green 144A in middle, then Yellow Green 145D on bottom ⅓); corollas 4 mm long and 1.5 mm wide, tubular, 5 lobed, glabrous, Yellow Green 147D; pistil 10 mm long, ovary 5 mm long, White 155A, style 4 mm long Yellow Green 145D, 2-branched stigma spreading, Yellow Green 145D; stamen 4 mm long, filaments 2 mm long and Yellow Green 145D, anthers 2 mm long and Greyed Purple N186A, pollen Yellow Orange 18A.

*Phyllaries*.—In 4 leafy series, area grows to 30 mm wide and 10 mm deep, lobes lanceolate in shape, reflexed, grow to 15 mm long and 4 mm wide, Green 137A, margins strigose, tip acute, strigose on both sides.

*Receptacle*.—Grows to 10 mm wide and 10 mm deep, White 155B.

*Bloom period*.—July through October in Canby, Oreg.

*Fragrance*.—Excellent, floral.

*Lastingness*.—Each inflorescence lasts about two weeks in Canby, Oreg.

Seeds: 3 mm long and 2.5 mm wide, oval, Brown 200C.

*Fertility*.—Low.

Disease and pests: No pests or diseases have been observed on plants grown under commercial conditions in Canby, Oreg. No resistances are known.

I claim:

1. A new and distinct *Echinacea* plant as herein illustrated and described.

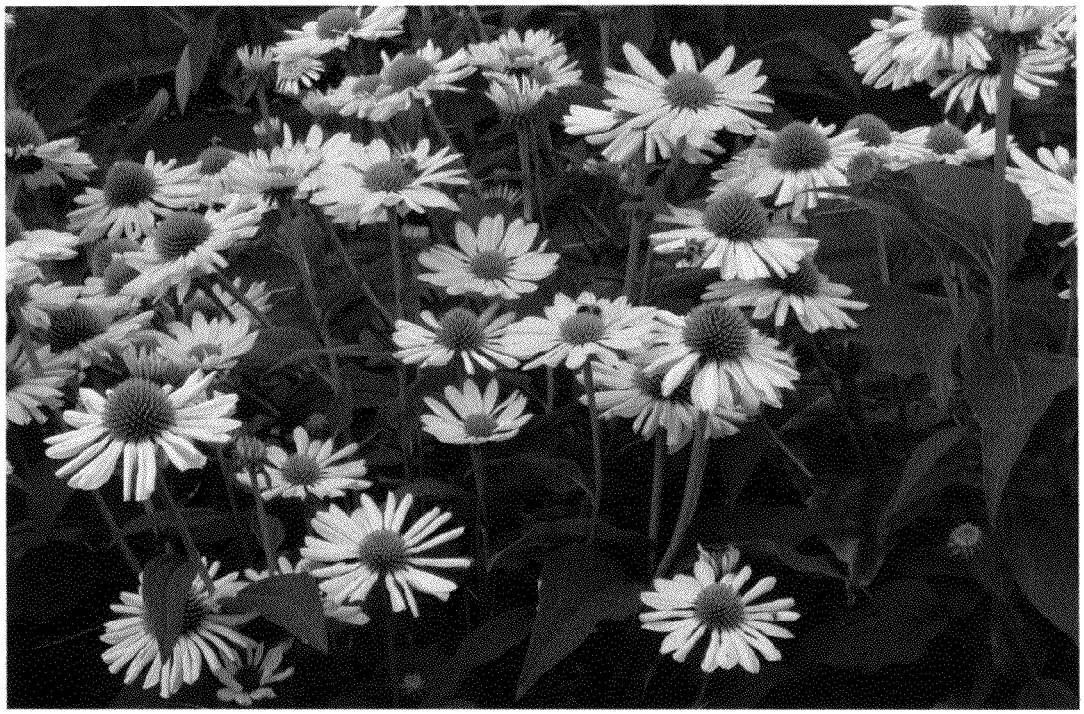

* * * * *